US009179883B2

(12) United States Patent
Spahn

(10) Patent No.: US 9,179,883 B2
(45) Date of Patent: Nov. 10, 2015

(54) X-RAY IMAGE ACQUISITION SYSTEM FOR DIFFERENTIAL PHASE CONTRAST IMAGING OF AN EXAMINATION OBJECT BY WAY OF PHASE STEPPING, AND ANGIOGRAPHIC EXAMINATION METHOD

(71) Applicant: SIEMENS AKTIENGESELLSCHAFT, Munich (DE)

(72) Inventor: Martin Spahn, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 62 days.

(21) Appl. No.: 14/102,690

(22) Filed: Dec. 11, 2013

(65) Prior Publication Data

US 2014/0177795 A1 Jun. 26, 2014

(30) Foreign Application Priority Data

Dec. 21, 2012 (DE) ......................... 10 2012 224 258

(51) Int. Cl.

*A61B 6/00* (2006.01)
*G01T 1/20* (2006.01)
*G01T 1/24* (2006.01)

(52) U.S. Cl.

CPC ............... *A61B 6/484* (2013.01); *A61B 6/4233* (2013.01); *A61B 6/4458* (2013.01); *A61B 6/504* (2013.01); *G01T 1/2006* (2013.01); *G01T 1/247* (2013.01);

(Continued)

(58) Field of Classification Search

CPC ........ A61B 6/484; A61B 6/502; A61B 6/503; A61B 6/504; G21K 1/06; G21K 7/00; G21K 2207/005

See application file for complete search history.

(56) References Cited

U.S. PATENT DOCUMENTS

| | | | |
|---|---|---|---|
| 5,812,629 | A | 9/1998 | Clauser |
| 7,500,784 | B2 | 3/2009 | Grebner et al. |

(Continued)

FOREIGN PATENT DOCUMENTS

| | | | |
|---|---|---|---|
| DE | 102006017290 | A1 | 8/2007 |
| DE | 102010018715 | A1 | 11/2011 |
| DE | 102011082878 | A1 | 3/2013 |
| EP | 2633813 | A1 | 9/2013 |
| WO | WO 2012052881 | A1 | 4/2012 |
| WO | WO 2012147528 | A1 | 11/2012 |

OTHER PUBLICATIONS

Martin Spahn, Volker Heer & Rudolf Freytag; "Flachbilddetektoren in der Röntgendiagnostik", Der Radiologe, vol. 43 (2003). pp. 340-350; 2003; DE.

(Continued)

*Primary Examiner* — Thomas R Artman

(74) *Attorney, Agent, or Firm* — Harness, Dickey & Pierce

(57) ABSTRACT

In an embodiment of an X-ray image acquisition system, an X-ray image detector includes a detector layer having a matrix composed of x total pixels structured in such a way that in a direction standing perpendicularly with respect to the grating lines of the diffraction or phase grating, the total pixels are subdivided into y subpixels which can be driven and/or read out in groups in a readout process such that, in a first phase step, n subpixels are effectively combined into groups, with m subpixels of a total pixel between the groups not being captured, and such that, in subsequent K−1 phase steps, n subpixels are in each case combined again into groups until all necessary combinations of subpixels have been captured, with the combined subpixels being shifted in the analysis direction by an increment of p subpixels in each case.

24 Claims, 7 Drawing Sheets

(52) U.S. Cl.
CPC ............. *A61B 6/4241* (2013.01); *A61B 6/4291* (2013.01); *A61B 6/4441* (2013.01); *A61B 6/5205* (2013.01)

(56) References Cited

U.S. PATENT DOCUMENTS

| | | | | |
|---|---|---|---|---|
| 8,576,983 | B2 * | 11/2013 | Baeumer et al. | 378/62 |
| 2007/0183581 | A1 | 8/2007 | Heismann et al. | |
| 2010/0246765 | A1 | 9/2010 | Murakoshi et al. | |
| 2010/0322380 | A1 * | 12/2010 | Baeumer et al. | 378/62 |
| 2011/0235775 | A1 | 9/2011 | Tada | |
| 2013/0208864 | A1 * | 8/2013 | Rossi | 378/62 |
| 2013/0235973 | A1 | 9/2013 | Murakoshi et al. | |
| 2014/0177795 | A1 * | 6/2014 | Spahn | 378/62 |

OTHER PUBLICATIONS

F. Pfeiffer, M. Bech, O. Bunk, P. Kraft, E. F. Eikenberry, Ch. Brönnimann, C. Grijnzweig and C. David; Hard X-ray dark-field imaging using a grating interferometer, Nature Materials, vol. 7, pp. 134-137; Feb. 1, 2008.

Joseph Zambelli, Nicholas Bevins, Zhihua Qi and Guang-Hong Chen; "Radiation dose efficiency comparison between differential phase contrast CT and conventional absorption CT"; Medical Physics, Jun. 2010, vol. 37, No. 6, pp. 2473-2479,; 2010.

* cited by examiner

X-RAY IMAGE ACQUISITION SYSTEM FOR DIFFERENTIAL PHASE CONTRAST IMAGING OF AN EXAMINATION OBJECT BY WAY OF PHASE STEPPING, AND ANGIOGRAPHIC EXAMINATION METHOD

PRIORITY STATEMENT

The present application hereby claims priority under 35 U.S.C. §119 to German patent application number DE 10 2012 224258.9 filed Dec. 21, 2012, the entire contents of which are hereby incorporated herein by reference.

FIELD

At least one embodiment of the invention generally relates to an X-ray image acquisition system for differential phase contrast imaging of an examination object, the system comprising at least an X-ray emitter for generating quasi-coherent X-ray radiation, an X-ray image detector having pixels arranged in a matrix, and a diffraction or phase grating which is arranged between the examination object and the X-ray image detector.

BACKGROUND

Differential phase contrast imaging constitutes an imaging method which in particular in the Talbot-Lau interferometer arrangement has for some time now been receiving a great deal of attention. Thus, for example, it is described in the publication by F. Pfeiffer et al. [1], "Hard X-ray dark-field imaging using a grating interferometer", Nature Materials 7, pages 134 to 137, that the use of X-ray optical gratings permits on the one hand the acquisition of phase-contrast X-ray images that provide additional information about an examination object. On the other hand it is also possible to use not just the phase information but also the amplitude information of scattered radiation for imaging. This enables an imaging modality to be created which is based exclusively on the scatter fractions of the X-ray radiation diffracted by the examination object, in other words a small-angle scattering technique. As a result, very small differences in density in the examination object can be visualized at very high resolutions. Similar findings are also revealed in Joseph J. Zambelli et al. [2], "Radiation dose efficiency comparison between differential phase contrast CT and conventional absorption CT", Med. Phys. 37 (2010), pages 2473 to 2479.

The wave nature of particles such as X-ray quanta allows phenomena such as diffraction and reflection to be described with the aid of the complex diffraction index $$n=1-\delta+i\beta,$$

where the imaginary part β describes the absorption on which contemporary clinical X-ray imaging such as e.g. that of computed tomography, angiography, radiography, fluoroscopy or mammography is based, and the real part δ describes the phase shift that is considered in differential phase imaging.

An X-ray image acquisition system is known from DE 10 2010 018 715 A1, wherein in order to achieve high-quality X-ray imaging use is made of an X-ray image acquisition system for phase contrast imaging of an examination object which has at least an X-ray emitter having a plurality of field-emission X-ray sources for emitting coherent X-ray radiation, an X-ray image detector, a diffraction grating $G_1$ arranged between the examination object and the X-ray image detector, and a further grating $G_2$ which is arranged between the diffraction grating $G_1$ and the X-ray image detector.

An X-ray image acquisition system by which differential phase contrast imaging of the type cited in the introduction can be performed is known for example from U.S. Pat. No. 7,500,784 B2, which system is explained with reference to FIG. 1.

FIG. 1 shows the typical essential features of an X-ray image acquisition system for an interventional suite, comprising a C-arm 2 which is supported by a stand 1 in the form of a six-axis industrial or articulated-arm robot and at the ends of which an X-ray radiation source, for example an X-ray emitter 3 comprising X-ray tube and collimator, and an X-ray image detector 4 are mounted as the image acquisition unit.

By way of the articulated-arm robot, known for example from U.S. Pat. No. 7,500,784 B2, which preferably has six axes of rotation and consequently six degrees of freedom, the C-arm 2 can be moved arbitrarily in three dimensions, for example by its being rotated about a center of rotation between the X-ray emitter 3 and the X-ray detector 4. The inventive angiographic X-ray system 1 to 4 can be rotated in particular about centers of rotation and axes of rotation in the C-arm plane of the X-ray image detector 4, preferably about the axes of rotation intersecting the center point of the X-ray image detector 4 and the center point of the X-ray image detector 4.

The known articulated-arm robot has a base frame which is permanently installed on a floor, for example. Secured thereto is a turntable which is rotatable about a first axis of rotation. Attached to the turntable so as to be capable of pivoting about a second axis of rotation is a robotic floating link to which a robotic arm is fixed so as to be rotatable about a third axis of rotation. A robotic hand is attached to the end of the robotic arm so as to be rotatable about a fourth axis of rotation. The robotic hand has a securing element for the C-arm 2 which can be pivoted about a fifth axis of rotation and rotated about a sixth axis of rotation running perpendicularly thereto.

The implementation of the X-ray diagnostic apparatus is not dependent on the industrial robot. Conventional C-arm devices can also be used.

The X-ray image detector 4 can be a flat semiconductor detector, rectangular or square in shape, which is preferably produced from amorphous silicon (a-Si). However, integrating and possibly counting CMOS detectors can also be used.

A patient 6 to be examined is positioned as the examination object in the beam path of the X-ray emitter 3 on a tabletop platform 5 of a patient examination table. Connected to the X-ray diagnostic apparatus is a system control unit 7 having an image system 8 which receives and processes the image signals of the X-ray image detector 4 (operator control elements, for example, are not shown). The X-ray images can then be studied on displays of a monitor array 9. Also provided in the system control unit 7 is a known device 10, the function of which will be described in greater detail.

Instead of the X-ray system having the stand 1 in the form of the six-axis industrial or articulated-arm robot shown by way of example in FIG. 1, the angiographic X-ray system can also have, as illustrated in simplified schematic form in FIG. 2, a normal ceiling- or floor-mounted support for the C-arm 2.

Instead of the C-arm 2 shown by way of example, the angiographic X-ray system can also have separate ceiling- and/or floor-mounted supports for the X-ray emitter 3 and the X-ray image detector 4 which are coupled for example in an electronically rigid manner.

In the arrangements for clinical phase contrast imaging that are the focus of attention today, use is made of conventional X-ray tubes, currently available X-ray image detectors, as described for example by Martin Spahn [3] in “Digitale Röntgenbilddetektoren in der Röntgendiagnostik” (“Digital X-ray image detectors in X-ray diagnostics”), Radiologe 43 (2003), pages 340 to 350, and three gratings $G_0$, $G_1$ and $G_2$, as will be explained in more detail hereinbelow with reference to FIG. 2, which shows a schematic layout of a Talbot-Lau interferometer for differential phase contrast imaging with extended tube focus, gratings $G_0$, $G_1$ and $G_2$, and pixelated X-ray image detector.

In order to generate coherent radiation, the X-rays 12 emitted from a tube focus 11 of the non-coherent X-ray emitter 3 penetrate an absorption grating 13 ($G_0$), which effects the spatial coherence of the X-ray radiation source, as well as an examination object 14, the patient 6 for example. In passing through the examination object 14 the wave front of the X-rays 12 is deflected by phase shifting, as illustrated by the normal 15 of the wave front without phase shift, i.e. without object, and the normal 16 of the wave front with phase shift. The phase-shifted wave front then travels through a diffraction or phase grating 17 ($G_1$) having a grating constant adapted to the typical energy of the X-ray spectrum for generating interference lines and in turn through an absorbing analyzer grating 18 ($G_2$) for reading out the generated interference pattern. The grating constant of the analyzer grating 18 is correlated with that of the phase grating 17 and the remaining geometry of the arrangement. The analyzer grating 18 is arranged e.g. at the first or n-th Talbot distance. In this case the analyzer grating 18 converts the interference pattern into an intensity pattern which can be measured by the detector. Typical grating constants for clinical applications are in the region of a few μm, as is also supported for example by the cited literature references [1, 2].

If the tube focus 11 of the radiation source is sufficiently small and the generated radiated power is nonetheless sufficiently great, it may be possible to dispense with the first grating $G_0$, the absorption grating 13, as is the case for example when a plurality of field-emission X-ray sources are provided as the X-ray emitter 3, as is known from the below-described DE 10 2010 018 715 A1.

The differential phase shift is now determined for each pixel of the X-ray image detector 4 in that by way of what is termed “phase stepping” 19, as indicated by an arrow, the analyzer grating 18 $G_2$ is shifted in multiple increments by a corresponding fraction of the grating constant vertically with respect to the radiation direction of the X-rays 12 and laterally with respect to the arrangement of the grating structure and the signal $S_k$ resulting for this configuration during the image acquisition in the pixel of the X-ray image detector 4 is measured and hence the resulting interference pattern sampled. The parameters of a function describing the modulation (e.g. sinusoidal function) are then determined for each pixel by means of a suitable fit method, an adaptation or compensation method, to the thus measured signals $S_k$. The visibility, i.e. the normalized difference formed from maximum and minimum signal, is in this case a metric for characterizing the quality of a Talbot-Lau interferometer. It is defined as the contrast of the sampled modulation $$V = \frac{I_{max} - I_{min}}{I_{max} + I_{min}} = \frac{A}{\bar{I}}.$$

Also in this equation, A denotes the amplitude and $\bar{I}$ the average intensity. The visibility can assume values between zero and one, since all variables are positive and $I_{max} > I_{min}$. In a real interferometer it also holds that $I_{min} > 0$, thereby beneficially exhausting the value range of V. Minimum intensities greater than zero and all non-ideal characteristics and defects of the interferometer lead to a reduction in visibility. A third item of information which can be defined via the visibility and is generated by this type of measurement is referred to as a dark field. The dark field specifies the ratio formed from the visibilities of the measurement with object and those without object.

$$D = \frac{V_{obj}}{V_{ref}} = \frac{A_{obj} \cdot \bar{I}_{ref}}{A_{ref} \cdot \bar{I}_{obj}}$$

Three different images can then be generated from the comparison of specific derived variables from the fitted functions for each pixel once with and once without object (or patient):

absorption image, differential phase contrast (DPC) image and dark-field image.

When reference is made hereinbelow to image, it may be that what is meant is the triumvirate formed from absorption, DPC and dark-field image.

The realization of the method poses many challenges, but in particular has one quite critical disadvantage:

The analyzer grating 18 $G_2$ must be maneuvered into different positions and an X-ray acquisition must then be performed in each position. It is therefore apparent that such a method is highly unsuitable for moving objects (such as non-anesthetized patients or patient organs, e.g. heart, lung), even if the object moves by only slight distances between the different measurements. Such a layout is likewise unsuitable due to the mechanical displacement of the analyzer grating 18, the phase stepping 19, to allow realtime imaging or imaging at higher image frame rates of e.g. 15 frames per second (fps) or even 60 to 100 fps. 3D imaging, in which X-ray emitter 3 with X-ray tube and X-ray image detector 4 is continuously rotated around the patient 6, is also not possible in this way.

It is described in EP 2 633 813 A1 that an interference pattern is produced by means of a relative rotation of the gratings $G_1$ and $G_2$ through an angle (Θ) in the vertical direction with respect to the grating lines. This results for example in M=5 interference fringes within a pixel structure D. In the corresponding direction, i.e. perpendicularly to the grating lines, the readout of the detector is then also driven with a subpixel size of Dy=D/M. The subpixel structure Dy is therefore in the order of magnitude of ⅕ of the pixel size D.

Also described is an analog readout of the detector by means of a light source/laser whose beam width is given precisely by Dy, where Dy has much greater dimensions than the grating structure.

SUMMARY

At least one embodiment of the invention is based on an X-ray image acquisition system which makes realtime-capable phase contrast imaging at high image frame rates possible, wherein the X-ray image detector has a layout which provides no mechanical movement of the analyzer grating $G_2$ or of the X-ray image detector.

At least one embodiment of the invention is directed to an X-ray image acquisition system. Advantageous embodiments are defined in the dependent claims.

At least one embodiment of an X-ray image acquisition system includes an X-ray image detector including a detector layer having a matrix composed of x total pixels which is structured in such a way that in an analysis direction standing perpendicularly with respect to the grating lines of the diffraction or phase grating $G_1$ the total pixels are subdivided into y subpixels which can be driven and/or read out in groups in a readout process in such a way that in a first phase step n subpixels are effectively combined into groups, with m subpixels of a total pixel between the groups not being captured, and that in subsequent K−1 phase steps n subpixels are in each case combined again into groups until all necessary combinations of subpixels have been captured, with the combined subpixels being shifted in the analysis direction by an increment of p subpixels in each case.

At least one embodiment of the invention is directed to an angiographic patient examination method including X-ray image acquisition system, such as the above-cited X-ray image acquisition system for example, for non-destructive readout of the image information of the X-ray image detector the method comprising:

S1) performance of an X-ray acquisition,
S2) iterative definition of combined pixels formed from total pixels and subpixels,
S3) non-destructive readout of the image information of the X-ray image detector,
S4) determination, in a first query, whether all necessary combinations of total pixels and subpixels have been reached,
S5) if no, return to S2) and repeated iterative definition of combined pixels formed from total pixels and subpixels,
S6) if yes, performance of image processing,
S7) determination, in a second query, whether still further images are required,
S8) if yes, return to S1) and repeated X-ray acquisition, and
S9) if no, initiation of the end of the process and termination of data acquisition.

At least one embodiment of the invention is directed to an angiographic patient examination method including X-ray image acquisition system, such as the above-cited X-ray image acquisition system for example, for non-non-destructive readout of the image information of the X-ray image detector, the method comprising:

S1) performance of an X-ray acquisition,
S2) iterative definition of combined pixels formed from total pixels and subpixels,
S3) non-non-destructive readout of the image information of the X-ray image detector,
S4) determination, in a first query, whether all necessary combinations of total pixels and subpixels have been reached,
S5) if no, return to S1) and repeated X-ray acquisition,
S6) if yes, performance of image processing,
S7) determination, in a second query, whether still further images are required,
S8) if yes, return to S1) and repeated X-ray acquisition, and
S9) if no, initiation of the process end 43 and termination of data acquisition.

BRIEF DESCRIPTION OF THE DRAWINGS

The invention is explained in more detail hereinbelow with reference to example embodiments illustrated in the drawing, in which.

DETAILED DESCRIPTION OF THE EXAMPLE EMBODIMENTS

Figure 1:
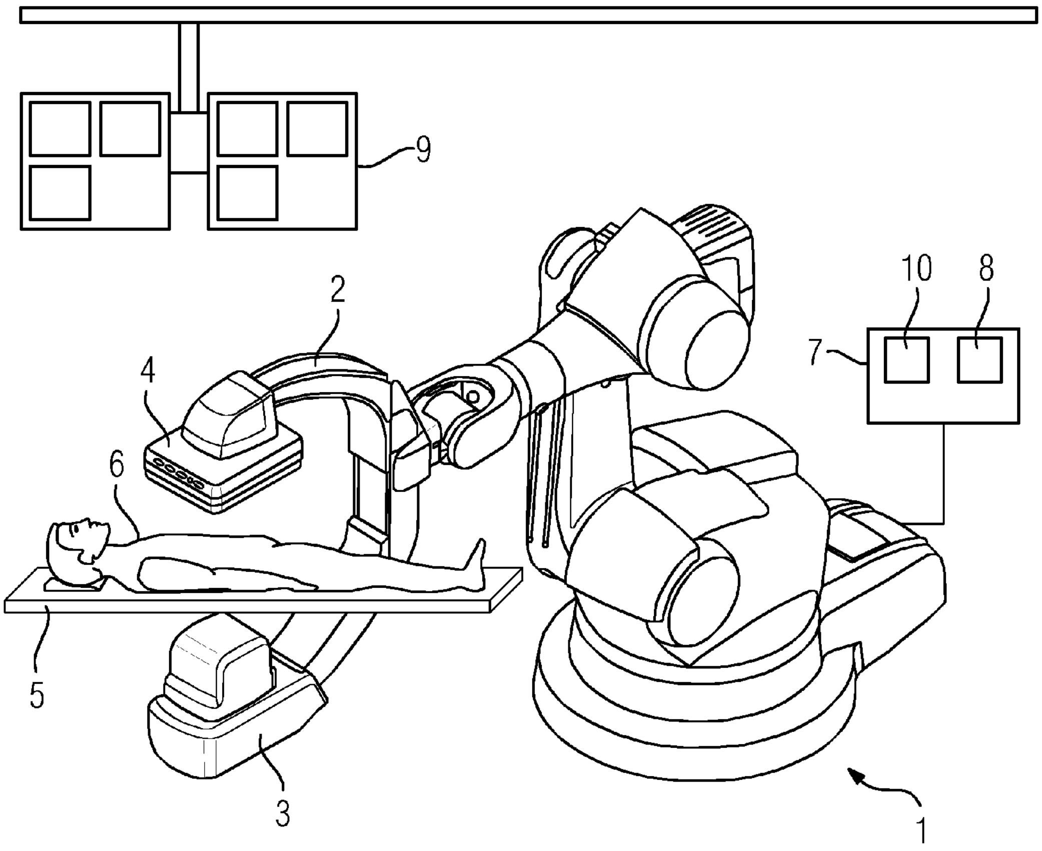
FIG. 1 shows a known C-arm angiography system of an interventional suite having an industrial robot as carrier device.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of an X-ray image acquisition system includes an X-ray image detector including a detector layer having a matrix composed of x total pixels which is structured in such a way that in an analysis direction standing perpendicularly with respect to the grating lines of the diffraction or phase grating $G_1$ the total pixels are subdivided into y subpixels which can be driven and/or read out in groups in a readout process in such a way that in a first phase step n subpixels are effectively combined into groups, with m subpixels of a total pixel between the groups not being captured, and that in subsequent K−1 phase steps n subpixels are in each case combined again into groups until all necessary combinations of subpixels have been captured, with the combined subpixels being shifted in the analysis direction by an increment of p subpixels in each case.

In at least one embodiment, the customary movement of the analyzer grating $G_2$ which samples the interference pattern is realized by different groupings of subpixels.

In this case the interference pattern which becomes established parallel to the grating lines is also measured. In other words, the grating lines of the gratings $G_1$ and $G_2$ are aligned parallel to one another and not rotated counter to one another in the x-y plane.

The resolution requirement placed on the X-ray image detector is in the order of magnitude of the primary interference patterns (or even higher), which in turn lie in the order of magnitude of the grating constants of the gratings $G_1$ and $G_2$.

A digital X-ray image detector is described here which is structured in a specific way, i.e. equipped with a subpixel resolution that is higher than the typical frequency of the interference pattern. Different subpixel structures are combined differently in each case and the combined signal is read out in each case in order to sample the interference pattern at said sampling points. The subpixels are grouped digitally.

It has proven advantageous if the X-ray emitter for generating quasi-coherent X-ray radiation has an absorption grating $G_0$.

The X-ray emitter for generating quasi-coherent X-ray radiation can advantageously have a plurality of field-emission X-ray sources or a sufficiently powerful microfocus source.

A rapid examination is made possible if in the readout process all subpixels are read out independently once and their output signals are stored, and the output signals of the subpixels are combined in groups in multiple phase steps, the combinations of the output signals of the subpixels being shifted in succeeding phases by p subpixels in the effective or analysis direction in each case.

Alternatively, adjacent subpixels can be combined in a total pixel in the readout process and the signals can be read out, the combinations of the output signals of the subpixels being shifted in succeeding phases by p subpixels in the effective or analysis direction in each case, or all subpixels of a total pixel that have been activated for a phase step are combined in the readout process and the total signal of all the required subpixels of the total pixel for said phase step is read out.

It has proven advantageous if the X-ray image detector is an integrating detector with indirect conversion of the X-ray quanta by means of CsI as detector material and CMOS for the photodiode and readout structure or is implemented as a photon-counting detector with direct conversion of the X-ray quanta.

At least one embodiment of the invention is directed to an angiographic patient examination method including X-ray image acquisition system, such as the above-cited X-ray image acquisition system for example, for non-destructive readout of the image information of the X-ray image detector the method comprising:

S10) performance of an X-ray acquisition,

S11) iterative definition of combined pixels formed from total pixels and subpixels, S12) non-destructive readout of the image information of the X-ray image detector, S13) determination, in a first query, whether all necessary combinations of total pixels and subpixels have been reached, S14) if no, return to S2) and repeated iterative definition of combined pixels formed from total pixels and subpixels, S15) if yes, performance of image processing, S16) determination, in a second query, whether still further images are required, S17) if yes, return to S1) and repeated X-ray acquisition, and S18) if no, initiation of the end of the process and termination of data acquisition.

At least one embodiment of the invention is directed to an angiographic patient examination method including X-ray image acquisition system, such as the above-cited X-ray image acquisition system for example, for non-non-destructive readout of the image information of the X-ray image detector, the method comprising:

S10) performance of an X-ray acquisition,

S11) iterative definition of combined pixels formed from total pixels and subpixels, S12) non-non-destructive readout of the image information of the X-ray image detector, S13) determination, in a first query, whether all necessary combinations of total pixels and subpixels have been reached, S14) if no, return to S1) and repeated X-ray acquisition, S15) if yes, performance of image processing, S16) determination, in a second query, whether still further images are required, S17) if yes, return to S1) and repeated X-ray acquisition, and S18) if no, initiation of the process end 43 and termination of data acquisition.

Figure 3:
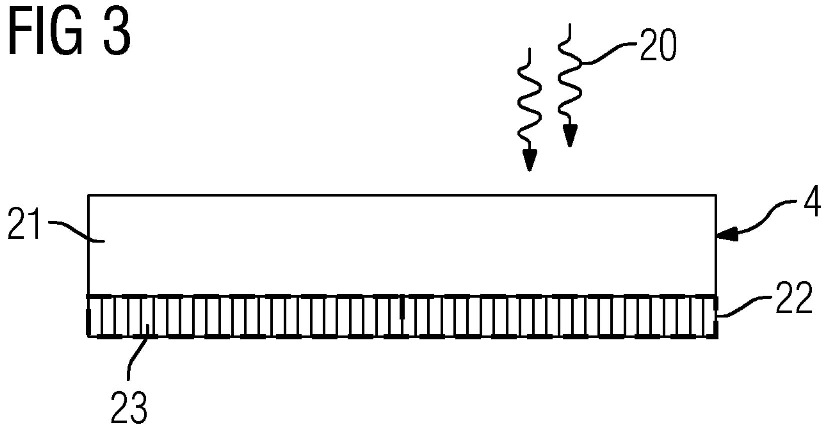
FIG. 3 is a schematic representation of a generic detector layout in a side view including a matrix of total pixels subdivided into subpixels.
Figure 4:
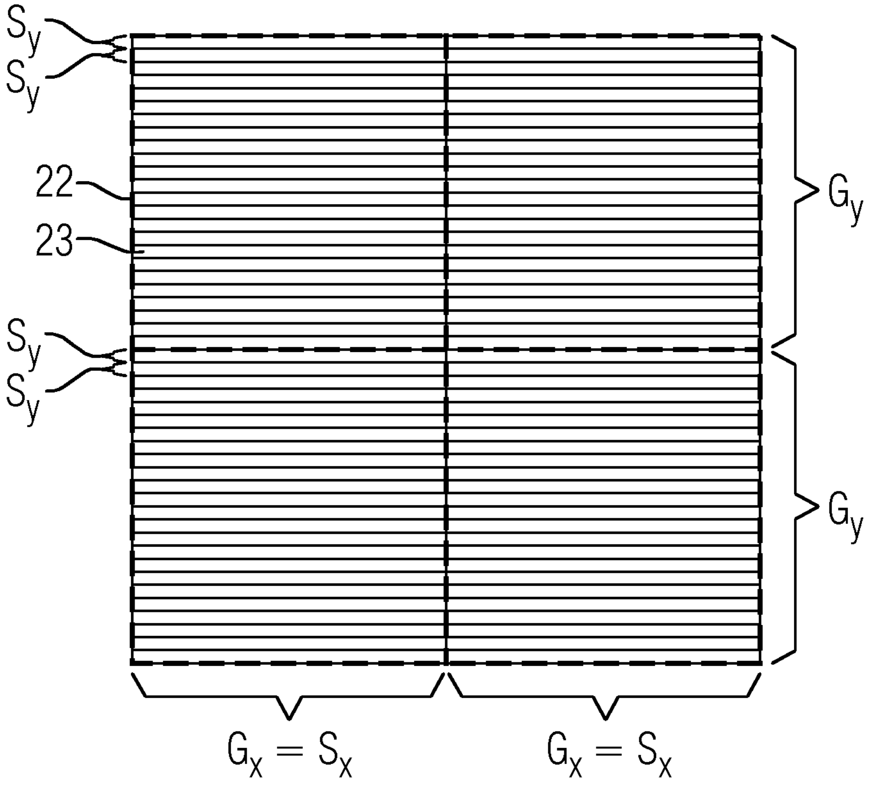
FIG. 4 shows the detector layout according to FIG. 3 in a plan view.

FIGS. 3 and 4 are schematic representations of a generic detector layout in a side view (FIG. 3) and plan view (FIG. 4). For conversion into visible light, the X-ray quanta 20 impinge onto an X-ray converter layer 21, behind which pixels 22 and 23 are arranged in a layer including a semiconductor material.

The structure of the pixels includes a matrix composed of total pixels 22 (represented by dashed lines) which are in turn subdivided into a plurality of subpixels 23 in a direction (effective or analysis direction) that stands perpendicularly with respect to the grating lines of the diffraction or phase grating 17. Laterally adjacent subpixels 23 (to right and left) can be arbitrarily combined with one another according to the invention, as will be described hereinbelow. The pixel structure sizes are designated by $G_x$ and $G_y$ in the x and y dimensions for the total pixels 22, and by $S_x$ and $S_y$ for the subpixels 23, where the dimensions $G_x$ and $S_x$ are the same.

Figure 5:
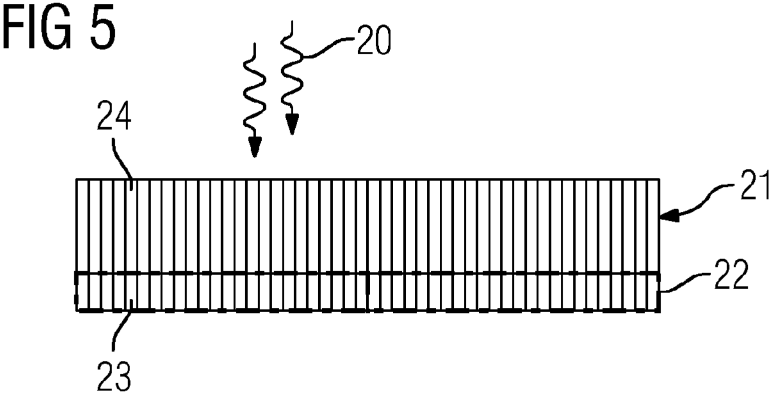
FIG. 5 is a schematic representation of a generic detector layout according to FIG. 3 with structured detector material, the structures of which are aligned to those of the subpixels.

FIG. 5 schematically represents an alternative generic detector layout to the embodiment variant according to FIG. 3 in a side view, in which, however, the X-ray converter layer 21 includes a structured detector material 24, the latter's structures being matched to those of the subpixels 23.

Figure 6:
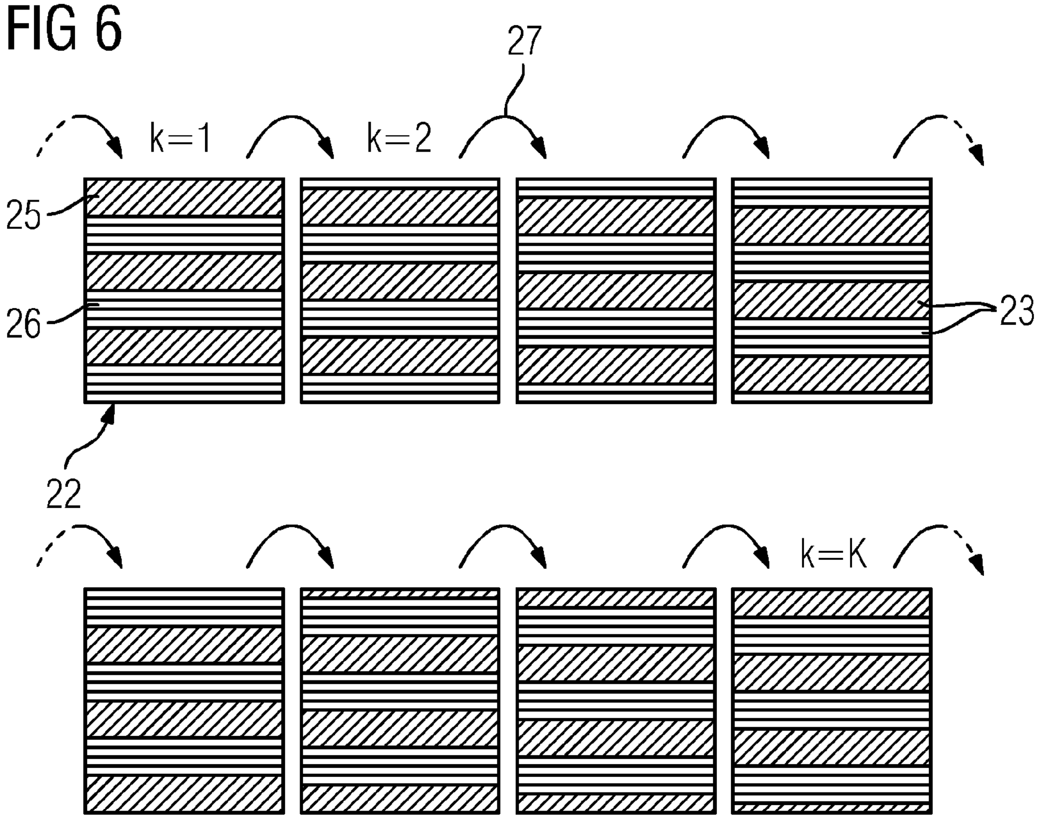
FIG. 6 is a schematic representation of the different combinations of subpixels of a total pixel in a plan view, intended to explain the phase stepping according to an embodiment of the invention.

FIG. 6 shows subpixels selected from the subpixels 23 of a total pixel 22 (or, as the case may be, of a part of a total pixel), the signals of which are read out for each electronic phase step and which henceforward are referred to as active or activated subpixels 25. The signals of the subpixels deselected for the current phase step 27, henceforward referred to as non-active subpixels 26, can be read out independently and/or combined in the pixel partially or else completely before the readout process is performed. The combined signals of all the selected active subpixels 25 of the total pixel 22 generate the pixel signal for this phase step k=1. Following the non-destructive readout, the subpixels 25 and 26 are combined anew in that all the active subpixels 25 are shifted by one subpixel 23. These are read out again in a phase step k=2. This process is repeated multiple times until the electronic phase stepping ($1 \le k \le K$) is terminated. In the above example, K=8 electronic phase steps 27 are performed.

In the "conventional" Talbot-Lau method, as explained with reference to FIG. 2, the analyzer grating $G_2$ (18) is shifted incrementally. The spatial frequency of these gratings is substantially higher than the spatial resolution of a pixel or, as the case may be, the grating spacing is substantially smaller (e.g. 2 or 3 μm) than the size of a pixel of a conventional X-ray image detector 4 which can be used there (for example 200 μm). The analyzer grating $G_2$ is shifted incrementally and in the process incrementally covers the interference pattern formed by the diffraction grating $G_1$.

In the present method, this is resolved in that the "normal" total pixel 22 (e.g. 200×200 $\mu m^2$) of the X-ray image detector 4 is subdivided into numerous strip-shaped subpixels 23 of, for example, 1 μm in width. Instead of the mechanical displacement of the analyzer grating $G_2$, which can be saved in the present case because it is no longer required, different subpixel ranges, each of which can includes one or more subpixels, are defined, read out and subsequently redefined.

In the example representation according to FIG. 6, therefore, a total pixel 22 having three groups of four active subpixels 25 and four non-active subpixels 26 in each case is subdivided. In the eight succeeding electronic phase steps 27, these three groups are moved downward by the width of the subpixels 23, resulting each time in a new combination (eight in total) of active subpixels 25 and non-active subpixels 26.

Realistically, with a subpixel width of, for example, 1 μm and a total pixel length of, for example, 200 μm, there are in the order of 50 to 100 groups of e.g. four subpixels 23, moving across the total pixel 22 in a plurality of phase steps.

The number of adjacent n subpixels 23 which are to be interconnected, or, as the case may, which range of m subpixels 23 is to be left free, is dependent on the width of the subpixels 23, which can of course amount for example to 0.5 μm, 1 μm, 1.5 μm or 2 μm. The number of active subpixels 25 is also dependent on how many electronic phase steps 27 are to be made. In this case a number of K=4 is seen as a minimum, and up to K=8 are used nowadays in order to have sufficient independent measurements for a curve fit with at least three variables. It is furthermore dependent on the spectrum: higher X-ray energies generate finer interference patterns because the quanta are deflected by small angles. In other words, for a given X-ray image detector 4 it may be necessary to limit n to three or two at high energies.

Finally it is the case that these days the grating constant of G2 is derived from the geometry, the spacings of $G_0$, $G_1$ and X-ray image detector 4. This is configured for a nominal X-ray energy. If other energies or wider spectra are used due to the application, the layout is suboptimal.

Accordingly, the layout of the X-ray image detector 4, i.e. in particular the width of the subpixels 23, must be based on the grating constant of the analyzer grating $G_2$, which is not present. Since the analyzer grating $G_2$ would be shifted per phase step by a fraction of its grating constant, which is assumed to be e.g. 5 μm, in other words e.g. by 0.5 to 1 μm, the subpixel width must correspondingly also be roughly of this size.

Figure 7:
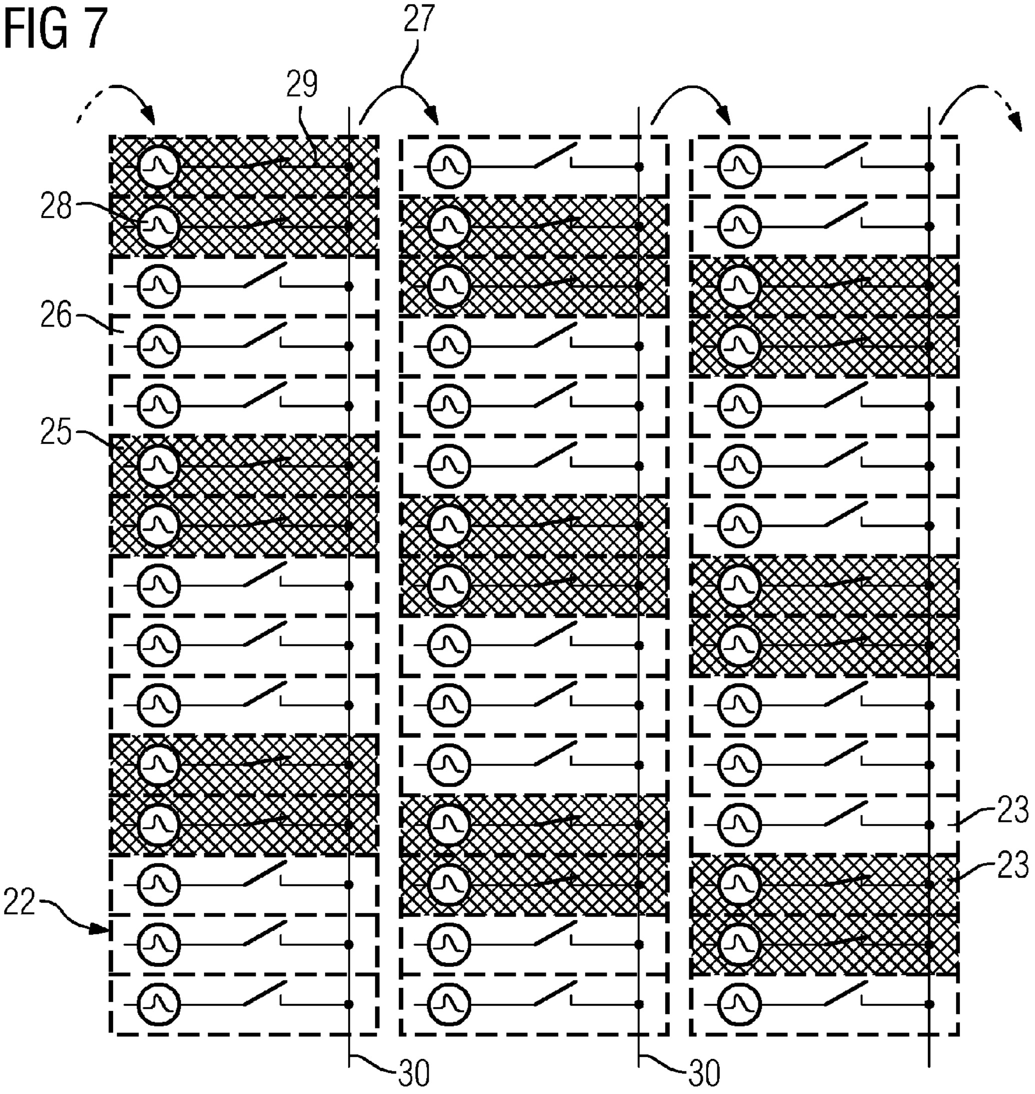
FIG. 7 is a schematic representation of the interconnection circuitry of the subpixels of a total pixel with signal source and switching device in three succeeding phase steps.

FIG. 7 shows a schematic representation of the interconnection of adjacent subpixels 23 with signal source and switching device of a total pixel 22 (distorted due to the details and not true to scale). The signals of a signal source 28 of the active subpixels 25 (shown highlighted) of a total pixel 22 are read out in order to implement an electronic phase step 27 in that switches 29 connect the signal source 28 to readout or data lines 30. Three such succeeding phase steps and corresponding subpixel combinations are shown here. Three groups of two active subpixels 25 and three non-active subpixels 26 each, as well as three phase steps 27, are shown. For the complete phase stepping, however, K phase steps 27 are required, where k=1 to k=K, where e.g. K=4 to 8.

Figure 8:
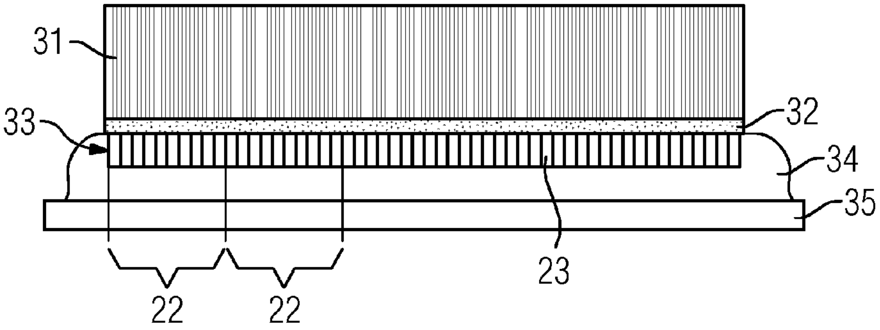
FIG. 8 shows an implementation as an integrating and indirectly converting X-ray image detector based on CsI and CMOS.

FIG. 8 shows an implementation as an integrating and indirectly converting X-ray image detector 4 based on caesium iodide (CsI) as detector material for the X-ray converter layer 21 and CMOS as semiconductor material for the pixels 22 and 23. The X-ray converter layer 21, a CsI layer 31, is connected to the CMOS pixel structure 33 by means of an optical coupling and adhesive layer 32 containing photodiodes, subpixel connections and readout electronics. The pixels 22 and 23 of the CMOS pixel structure 33 are connected to a peripheral detector electronics circuit 35 via electrical connections 34.

Figure 9:
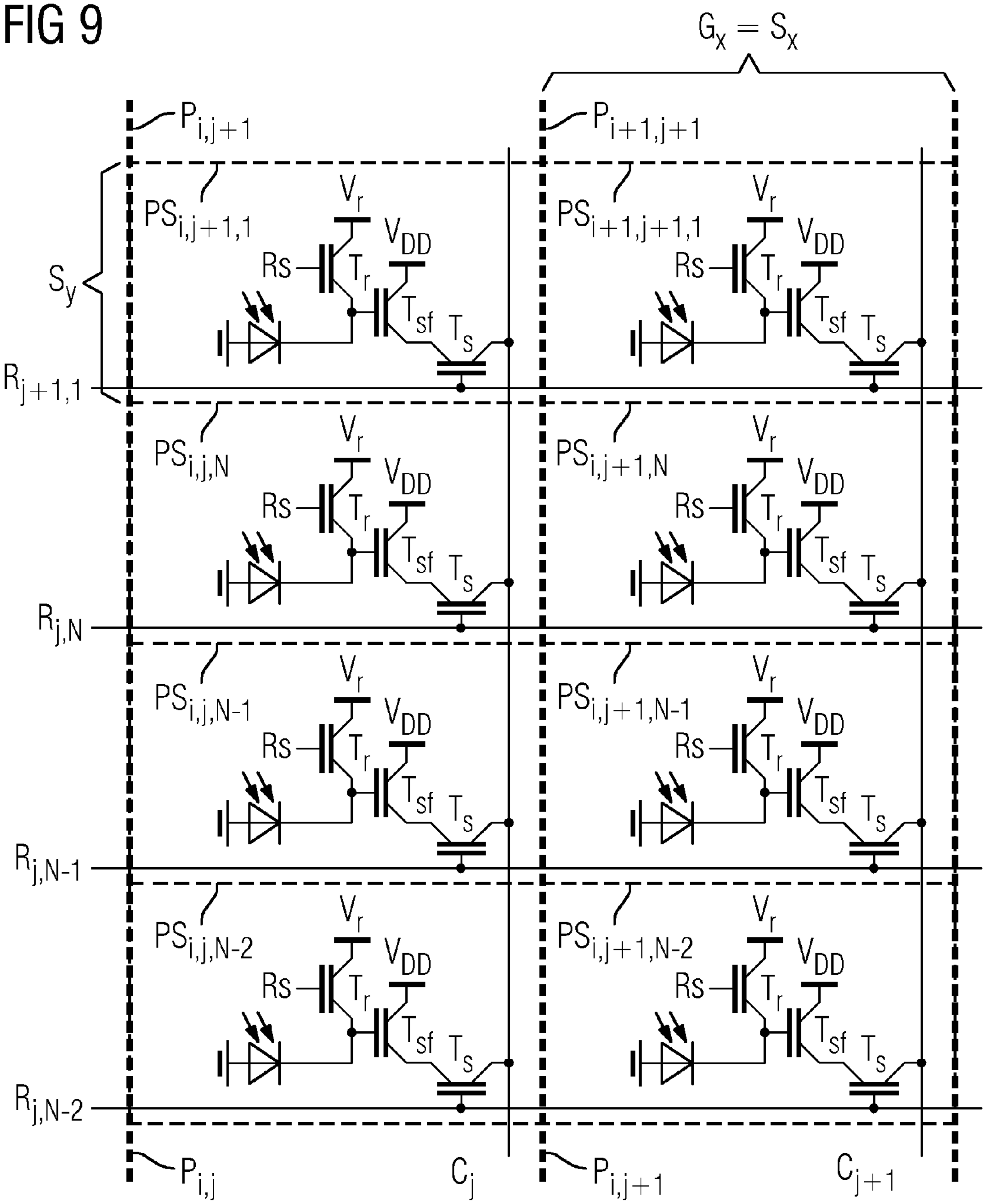
FIG. 9 is a schematic partial representation of four total pixels having subpixels implemented as a 3-transistor circuit.

FIG. 9 schematically shows a detail of an X-ray image detector 4 having four partially represented total pixels (P) with subpixels (PS) implemented as a 3-transistor circuit, wherein a transistor $T_r$ for resetting (Rs) the photodiode, a transistor $T_s$ for selecting the row(s) (R) and a transistor $T_{Sf}$ as source follower are provided for each pixel for the non-destructive readout of the signals in the column direction (C). The representation in the x- or y-direction is not true to scale. The total pixels 22 are designated by $P_{i,j}$ for the total pixel 22 in the i-th column $C_i$ and the j-th total pixel row $R_j$, the indices being incremented accordingly. The subpixels are designated by $PS_{i,j,N}$ for the subpixels in the i-th column $C_i$ and in the N-th total pixel of the j-th row $R_{j,N}$.

However, the total signal of the interconnected subpixels 23 that are assigned to a total pixel 22 can also be conducted to the periphery via a common line per total pixel 22. Equally, the subpixels 23 of a total pixel 22 could be driven by means of a drive device per total pixel 22.

Figure 10:
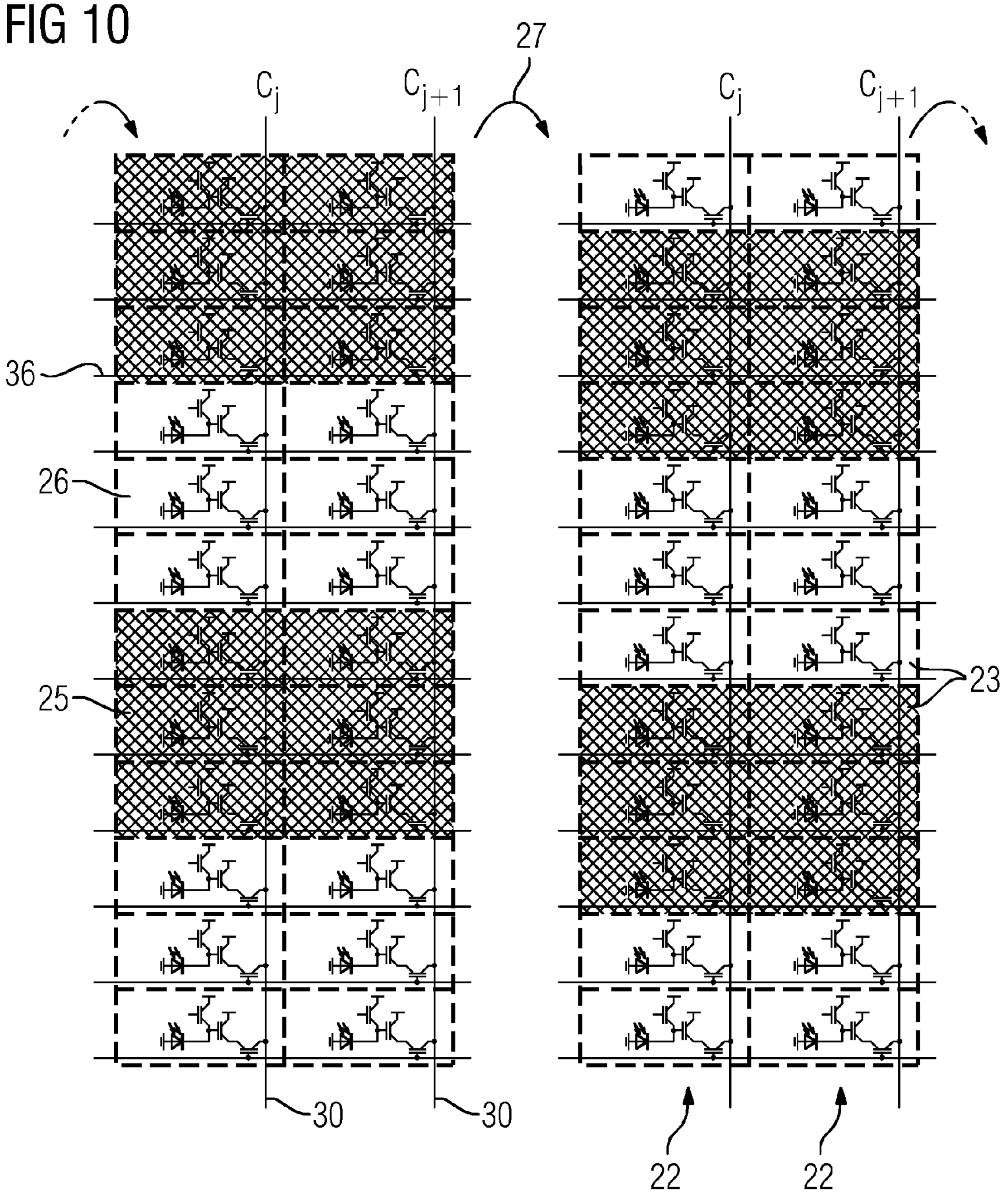
FIG. 10 is a representation of two total pixel structures or two parts of total pixel structures in a CMOS implementation.

FIG. 10 shows two phase steps 27 of two adjacent total pixel structures in the x-direction or of two parts of total pixel structures in a CMOS implementation, wherein an analog summation of the signals of the active subpixels 25 is generated by corresponding addressing of the rows via drive lines 36.

Two groups of three subpixels 25 in each case are shown, with three non-active subpixels 26 adjacent thereto. Generally this will only be an extract of two total pixels 22, since of course, as described above, realistically e.g. 200 subpixels 23 per total pixel 22 and e.g. 50 to 100 groups of active subpixels 25 per total pixel are required per phase step 27.

Figure 11:
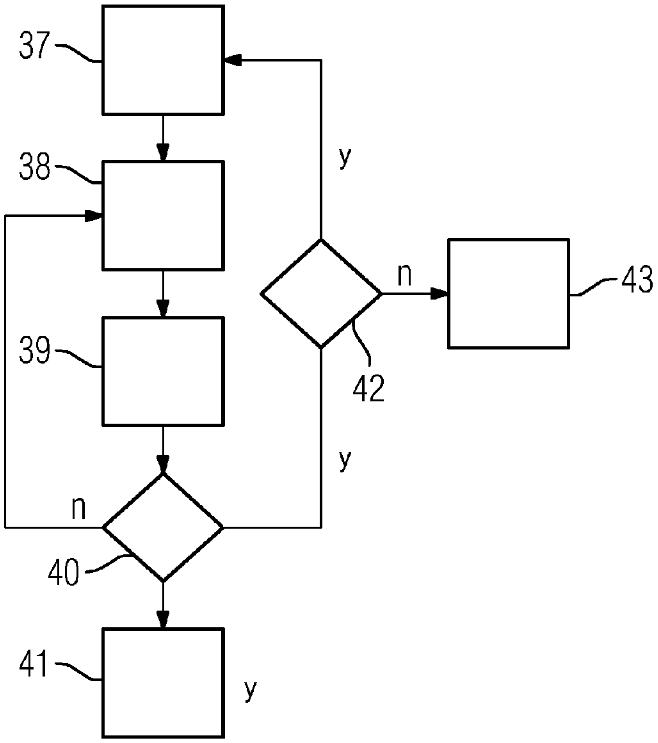
FIG. 11 is a flowchart of the X-ray acquisition, iterative definition of combined pixels formed from total pixels and subpixels, non-destructive readout of the image information, and image post-processing.

FIG. 11 shows a flowchart of an X-ray acquisition, iterative definition of combined pixels formed from total pixels and subpixels, and non-destructive readout of the image information and image post-processing.

Figure 2:
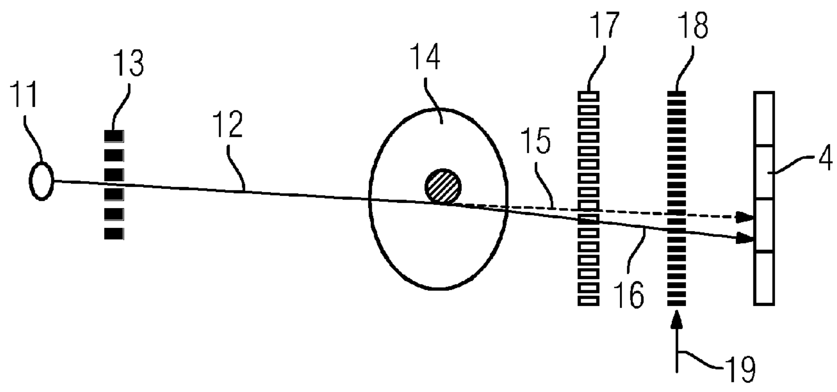
FIG. 2 shows a schematic layout of a known Talbot-Lau interferometer for differential phase contrast imaging.

In a first method step, an X-ray acquisition 37 takes place which is performed according to FIG. 2 with the exception of the missing analyzer grating 18 ($G_2$).

In a second method step, an iterative definition 38 of combined pixels formed from total pixels 22 and subpixels 23 is performed.

The third method step effects a non-destructive readout 39 of the image information.

In a first query 40 as fourth method step, it is determined whether all the necessary combinations of total pixels 22 and subpixels 23 have been reached.

In the case of a negative result, a return is made to the second method step and an iterative definition 38 of combined pixels formed from total pixels 22 and subpixels 23 is performed again. If the answer is yes, image processing 41 is first performed in a fifth method step.

Next, in a second query 42, it is determined whether still further images are required.

In the case of an affirmative result, a return is made to the first method step and a new X-ray acquisition 37 is performed. If the answer is no, the process end 43 is reached as the last method step and the data acquisition is terminated.

In this case the second method step again performs an iterative definition 38 of combined pixels formed from total pixels 22 and subpixels 23 according to the preceding figures with their description.

Figure 12:
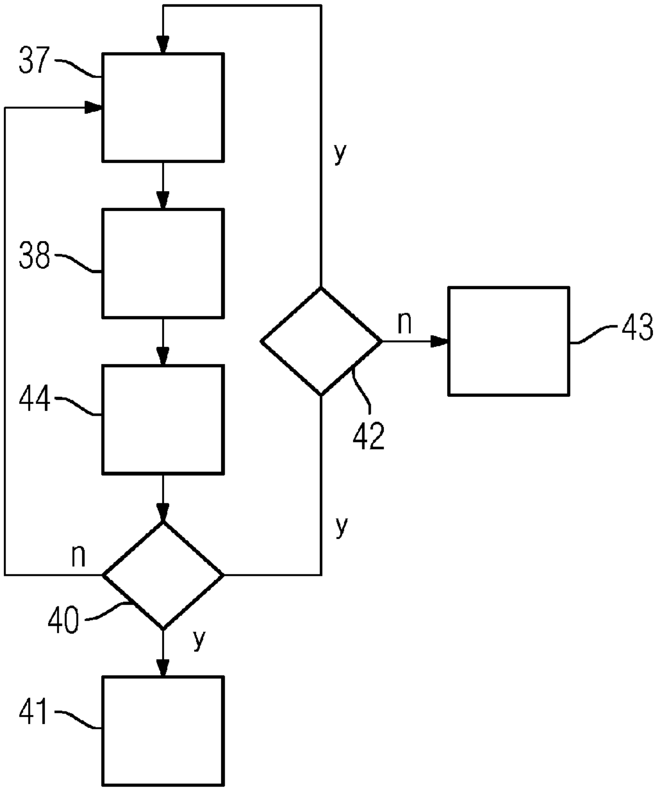
FIG. 12 is a flowchart of the X-ray acquisition, iterative definition of combined pixels formed from total pixels and subpixels, readout of the image information, and image post-processing for the case of a non-non-destructive readout.

FIG. 12 shows a flowchart of the X-ray acquisition 37, iterative definition of combined pixels formed from total pixels and subpixels, and the readout of the image information and image post-processing for the case of a non-non-destructive readout.

The main difference compared to the method flow sequence according to FIG. 11 is the third method step, in which a non-non-destructive readout 44 of the image information is performed. As a consequence thereof, after the readout 44 following a negative first query 40, a new X-ray acquisition 37 must be performed with the following method steps.

An embodiment of the present invention relates to an X-ray image acquisition system having an X-ray image detector for realtime-capable differential phase contrast imaging of an examination object at high image frame rates by way of what is termed "electronic" phase stepping.

However, instead of a mechanical movement of the analyzer grating $G_2$, as is known for example from DE 10 2010 018 715 A1, a suitable detector layout and an electronic method of driving the X-ray image detector in connection with the X-ray acquisition are proposed according to an embodiment of the invention.

Specifically, the advantages of "electronic" phase stepping are:

- It enables realtime imaging and high image frame rates.
- It can be implemented with currently available technology, e.g. CsI and CMOS.
- With this layout, no mechanical movements are required, because the phase stepping is implemented electronically.
- The complexity of the X-ray image detector is manageable compared to currently available X-ray image detectors.
- In an implementation variant (realization as indirectly converting, integrating X-ray image detector), the currently typical layout of the detection layer or detector layer (e.g. CsI) can essentially be used, since only the photodiode structure needs to be adapted. In other words, no structuring of the X-ray converter at all is necessary, in contrast to what is already customary today (needle structure, in order to obtain good MTF and DQE).
- Systematic "errors", due, for example, to a lower fill factor (relative proportion of the photodiode in the pixel size) of the subpixel structures compared to the total pixel structure, are ruled out, since the total pixel is always made up of the same number of subpixels and only the "position" is changed.
- In the preferred implementation in CMOS with "non-destructive readout", only one X-ray acquisition is required. The signals of the total pixels and subpixels stored in the CMOS photodiodes can be recombined in each case in order to generate the signal of the thus defined total pixel and read out said signal non-destructively. Owing to the non-destructive readout, this "total pixel definition process" and readout process can therefore be repeated multiple times without a new X-ray acquisition.

The following considerations are presented initially in relation to known layouts that provide one-dimensional gratings, as have been considered for example in the cited literature [1, 2].

Implementation Examples

The above-described FIGS. 3 to 8 show relatively generic representations of the X-ray image detector 4. The representation according to FIG. 3 does not deal therein with the readout process, but merely shows the structure of the X-ray image detector 4, which includes a matrix of total pixels 22 which are in turn subdivided into many subpixels 23, the subdivision, as also that of the gratings $G_0$, $G_1$ or $G_2$, being one-dimensional, as is the case generally with the Talbot-Lau method. According to the invention, the grating $G_2$ is intended to be replaced. The extension of the subpixels 23 in the direction standing perpendicularly with respect to the grating lines of the diffraction or phase grating 17 (effective or analysis direction) therefore describes both analog and digital electronic phase stepping.

The signals of the subpixels 23 required for a given electronic phase step can be read out in a variety of variants:

a. An independent readout for each subpixel 23; the signals are then combined outside of the detector matrix. In this case a readout must be performed only once, since the different phase steps can be represented peripherally through combination of the corresponding subpixel signals.

b. Adjacent subpixels 23 in a total pixel 22 can be combined and these signals read out (in FIGS. 5 and 6 that would be three and four subpixel ranges, respectively, for each electronic phase step 27, which are read out for each pixel separately). The read-out combined signals of adjacent subpixels 23 of a total pixel 22 are combined outside of the detector matrix into a total pixel signal for said electronic phase step 27.

c. All subpixels 25 of a total pixel 22 that have been activated for the current phase step 27 are combined and the total signal of all required subpixels 25 of the total pixel 22 for said electronic phase step 27 is read out.

It is initially not defined more precisely whether the combination in b) or c) of certain subpixels is performed in an analog or digital manner. What is important, however, is that because of the multiple readout and/or combining of subpixels 23 in the total pixel 22 the readout process can be performed non-destructively.

Applications are conceivable for mammography, general radiography, angiography, computed tomography, etc. Two typical examples are given below.

The pixel structure sizes for the total pixels 22 are designated by $G_x$ and $G_y$ in the x and y dimensions, and by $S_x$ and $S_y$ for the subpixels 23. The size of the total pixels 22 is dependent on the application, for example i. $G_x=G_y=50$-100 μm for mammography, ii. $G_x=G_y=130$-200 μm for applications from radiography, angiography, surgery, or iii. $G_x=G_y=300$-1000 μm for applications from computed tomography or flat-panel cone-beam CT.

The values are merely reference points and can lie above or below those cited.

The extension of the subpixels 23 in the analysis direction (in the x-direction in FIGS. 3 and 5, in the y-direction in FIG. 4) is dependent inter alia on the application, the X-ray spectrum, the geometry of the layout of X-ray tube, grating and X-ray image detector, the chosen gratings, in particular $G_1$, and the number of electronic phase steps required. A typical order of magnitude of $S_y$ amounts to approximately 1 m. The value can also lie above or below this, however. With one-dimensional gratings the other dimension, $S_x$, agrees with $G_x$.

FIG. 5 shows a detector layout in which the structure of the detector material 24 is matched to that of the subpixels 23. This can be of advantage in order to avoid or reduce crosstalk between signals.

The inventive interconnection circuitry and driving of the subpixels 23 of a total pixel 22 (or of the part of a total pixel 22) of an embodiment was explained with reference to FIG. 6, in which the output signal of the active subpixels 25 for each electronic phase step 27 is read out. The output signals of the deselected, non-active subpixels 26 for the current phase step 27 can be read out independently and combined in the pixel partially or else completely before the readout process is performed. The combined output signal of all active subpixels 25 of a total pixel 22 generates the pixel signal for said phase step 27. Following the non-destructive readout, the subpixels 23 are recombined and read out once more. The process is repeated multiple times until the electronic phase stepping is terminated. In the above example K=8 electronic phase steps 27 are performed.

FIG. 7 showed an interconnection of the subpixels 25 with signal source and switching device in a schematic representation. The signals of the active subpixels 25 of a total pixel 22 are read out in each case in order to realize an electronic phase step 27. In this example three such phase steps and corresponding subpixel combinations are shown.

It was shown with reference to FIGS. 6 and 7 how the electronic phase stepping 27 is performed by appropriate selection of subpixels 25. A plurality of subpixel combinations and a plurality of readout processes are required in this case. It is therefore necessary for the signal to be able to be read out non-destructively. The cases b) and c) are therefore shown in which the phase stepping happens on the pixel (and not digitally outside of the detector as in a)).

The preferred embodiment or implementation is a realization as analog electronic phase stepping by way of an integrating and indirectly converting detector based on CsI as detector material and CMOS for the photodiode and readout structure, as has been explained for example with reference to FIGS. 8 and 9, since here

- currently common detector material (CsI) can be used. In other words, no structuring of the CsI layer at all is necessary (apart from the currently already customary needle structure for maximizing the modulation transfer function (MTF), though its structure does not correlate with the subpixel structure)—see also FIG. 8.
- CMOS allows small structures which are necessary in particular for the very small subpixels in order to maximize the photodiode.
- CMOS enables non-destructive readout and consequently supports multiple readouts with an in each case different combination of the signals of photodiodes of the subpixels.

Assume the detector to have a total pixel matrix composed of i=1 to I total pixels 22 in the x-direction and j=1 to J total pixels 22 in the y-direction. Let each total pixel 22 be subdivided into n=1 to N subpixels 23. A specific total pixel 22 is subscripted with $P_{i,j}$, a given subpixel 23 with $PS_{i,j,N}$.

FIG. 9 showed a partial representation of four total pixels 22 and parts of the corresponding subpixels 23 as a possible implementation of a variant of subpixel structures in CMOS in which each subpixel 23 possesses a photodiode and a readout circuit. The gate of the selection transistor $T_s$ is driven via the corresponding row ($R_j$). The signal of the subpixel (and of other selected subpixels of a total pixel $P_{i,j}$) is read out via the source follower $T_{sf}$. The readout process can take place for all columns (j=1 to J) simultaneously. The readout process is repeated for all subpixel combinations (electronic phase steps) for said row $R_j$. The next row $R_{j+1}$ is then read out. After all of the electronic phase steps have been read out, the photodiode is biased again with the aid of the reset transistor $T_r$.

Alternatively it is of course also possible firstly to read out a certain phase step for all rows and then the next phase step for all rows. The resetting of the photodiodes (application of the bias voltage) then takes place at the end.

FIG. 10 shows once again extracts of two total pixel structures or of two parts of total pixel structures with the subpixel structure implemented in CMOS and two electronic phase steps, wherein an analog summation of the signals of the subpixels is generated by corresponding addressing of the rows. Highlighted in this case are those subpixels 25 that have been driven via the corresponding rows and whose signals are read out via the column lines.

FIG. 11 shows a flowchart:

A first X-ray acquisition 37 is performed. A first combination of total pixels 22 and subpixels 23 is then formed and the thus defined total signal of the total pixel 22 read out non-destructively. This is repeated for all total pixels 22 defined in that way. A new total pixel 22 is subsequently defined from the corresponding combination of total pixels 22 and subpixels 23 and read out again. This is iterated according to the required number of electronic phase steps until all combinations have been completed. The thus generated images having different total pixels 22 are then supplied to the image processing entity 41 for the purpose of generating absorption, phase contrast and dark-field images. In the event of a second or further X-ray acquisitions 37 being performed, as is generally the case with moving objects, moving C-arm or moving contrast agent and/or guide wire, the entire process is iterated.

In the case of a detector design which does not support destructive readout, a plurality of X-ray acquisitions 37 must be performed in quick succession, wherein the desired total pixel structures must be defined by corresponding interconnection of the total pixels 22 and subpixels 23. Thus, for example, the photodiodes, in the case of an indirectly converting detector, or the electrodes, in the case of a directly converting detector, could be interconnected and the corresponding signals from the thus defined total photodiodes or total electrodes read out for each acquisition.

FIG. 12 shows a flowchart in this regard. Since the readout process is destructive, a new X-ray acquisition 37 must be performed for each combination of total pixels 22 and subpixels 23 and before each readout.

An alternative implementation would be not to combine the signals in an analog manner at pixel level, as assumed in connection with FIGS. 8 and 9, but to read out the signals of the total pixels 22 and subpixels 23 separately and to perform the different combinations only after the digitization. The advantage would be that only one X-ray acquisition 37 and one readout process per image are necessary. Admittedly, this solution initially has a disadvantage, since the signals of total pixels 22 and subpixels 23 are approximately in the ratio of the relative active surfaces (e.g. photodiode sizes in the case of integrating, indirectly converting detectors), i.e. approximately $S_y/G_y$ (e.g. a factor of roughly 1/100). Depending on structure sizes for the readout units and the actually active surface, this can assume other values also. In other words, much smaller signals would be generated for the subpixels 23, which would necessitate a very high digitization overhead. If, for example, a digitization of e.g. 18 bits would suffice for the total pixel, about 7 bits would be required in addition on account of the subpixels 23.

However, the following solution could eliminate the problem:

In the subpixel 23 provision is made to ensure that the signal is output amplified such that the loss due to the much smaller active surface of the subpixels 23 compared to the active surface of the total pixels 22 is roughly compensated for. In the case of a photodiode/CMOS-based design, as described in connection with FIGS. 8 and 9, it would be possible to achieve that by appropriate design of $T_{sf}$ (source follower). In that case, however, the amplification factor would have to be computationally eliminated again prior to combination, in other words generation of a total signal from the signals of total pixels 22 and subpixel(s) 23.

An advantage of an embodiment of this method would be that a readout would only have to be performed once, thereby enabling higher image frame rates to be achieved.

What is claimed is:

1. An X-ray image acquisition system for differential phase contrast imaging of an examination object, said system comprising:

at least an X-ray emitter configured to generate quasi-coherent X-ray radiation;

an X-ray image detector including pixels arranged in a matrix; and a diffraction or phase grating arranged between the examination object and the X-ray image detector, the X-ray image detector including a detector layer formed of a plurality of pixels in an analysis direction perpendicular to grating lines of the diffraction or phase grating, wherein during each iteration of a readout process, a first plurality of subgroups of the plurality of pixels are read out while a second plurality of subgroups of the plurality of pixels are not read, each of the second plurality of subgroups being interposed between two of the first plurality of subgroups, each of the first and second plurality of subgroups including at least one of the plurality of pixels, the first and second plurality of subgroups change in each iteration of the readout process compared to other iterations of the readout process, and the readout process is iteratively performed until all of the plurality of pixels are read out.

2. The X-ray image acquisition system of claim 1, wherein the X-ray emitter includes an absorption grating.

3. The X-ray image acquisition system of claim 2, wherein, in the readout process, all of the plurality of pixels are read out independently once and corresponding output signals are stored, and the output signals of the subpixels are combined into groups in multiple iterations of the readout process, combinations of the output signals being shifted in the analysis direction in succeeding phases by p pixels in each case, p being an integer equal to or greater than 1.

4. The X-ray image acquisition system of claim 2, wherein, in the readout process, adjacent pixels in each of the first plurality of subgroups are combined in a total pixel and corresponding output signals are read out, combinations of the output signals being shifted in the analysis direction in succeeding phases by p pixels in each case, p being an integer equal to or greater than 1.

5. The X-ray image acquisition system of claim 2, wherein, in the readout process, all of the plurality of pixels in each of the first plurality of subgroups form a total pixel that is activated, and a total signal of the total pixel is read out.

6. The X-ray image acquisition system of claim 2, wherein the X-ray image detector is an integrating detector with indirect conversion of X-ray quanta via CsI as detector material and CMOS for a photodiode and a readout structure configured to perform the readout process.

7. The X-ray image acquisition system of claim 2, wherein the X-ray image detector is implemented as a photon-counting detector with direct conversion of the X-ray quanta.

8. The X-ray image acquisition system of claim 1, wherein the X-ray emitter includes a plurality of field-emission X-ray sources.

9. The X-ray image acquisition system of claim 8, wherein, in the readout process, all of the plurality of pixels are read out independently once and corresponding output signals are stored, and the output signals of the subpixels are combined into groups in multiple iterations of the readout process, combinations of the output signals being shifted in the analysis direction in succeeding phases by p pixels in each case, p being an integer equal to or greater than 1.

10. The X-ray image acquisition system of claim 8, wherein, in the readout process, adjacent pixels in each of the first plurality of subgroups are combined in a total pixel and corresponding output signals are read out, combinations of the output signals being shifted in the analysis direction in succeeding phases by p pixels in each case, p being an integer equal to or greater than 1.

11. The X-ray image acquisition system of claim 8, wherein, in the readout process, all of the plurality of pixels in each of the first plurality of subgroups form a total pixel that is activated, and a total signal of the total pixel is read out.

12. The X-ray image acquisition system of claim 8, wherein the X-ray image detector is an integrating detector with indirect conversion of X-ray quanta via CsI as detector material and CMOS for a photodiode and a readout structure configured to perform the readout process.

13. The X-ray image acquisition system of claim 8, wherein the X-ray image detector is implemented as a photon-counting detector with direct conversion of X-ray quanta.

14. The X-ray image acquisition system of claim 1, wherein the X-ray emitter includes a microfocus source.

15. The X-ray image acquisition system of claim 1, wherein, in the readout process, all of the plurality of pixels are read out independently once and corresponding output signals are stored, and the output signals of the subpixels are combined into groups in multiple iterations of the readout process, combinations of the output signals being shifted in the analysis direction in succeeding phases by p pixels in each case, p being an integer equal to or greater than 1.

16. The X-ray image acquisition system of claim 1, wherein, in the readout process, adjacent pixels in each of the first plurality of subgroups are combined in a total pixel and corresponding output signals are read out, combinations of the output signals being shifted in the analysis direction in succeeding phases by p pixels in each case, p being an integer equal to or greater than 1.

17. The X-ray image acquisition system of claim 1, wherein, in the readout process, all of the plurality of pixels in each of the first plurality of subgroups form a total pixel that is activated, and a total signal of the total pixel is read out.

18. The X-ray image acquisition system of claim 1, wherein the X-ray image detector is an integrating detector with indirect conversion of X-ray quanta via CsI as detector material and CMOS for a photodiode and a readout structure configured to perform the readout process.

19. The X-ray image acquisition system of claim 1, wherein the X-ray image detector is implemented as a photon-counting detector with direct conversion of X-ray quanta.

20. An X-ray image detector for an X-ray image acquisition system, comprising:

a detector layer formed of a plurality of pixels in an analysis direction standing perpendicular with respect to grating lines of a diffraction or phase grating of the X-ray image acquisition system, wherein during each iteration of a readout process, a first plurality of subgroups of the plurality of pixels are read out while a second plurality of subgroups of the plurality of pixels are not read, each of the second plurality of subgroups being interposed between two of the first plurality of subgroups, each of the first and second plurality of subgroups including at least one of the plurality of pixels, the first and second plurality of subgroups change in each iteration of the readout process compared to other iterations of the readout process, and the readout process is iteratively performed until all of the plurality of pixels are read out.

21. The X-ray image detector of claim 20, wherein the X-ray image detector is an integrating detector with indirect conversion of the X-ray quanta via CsI as detector material and CMOS for a photodiode and a readout structure configured to perform the readout process.

22. The X-ray image detector of claim 20, wherein the X-ray image detector is implemented as a photon-counting detector with direct conversion of X-ray quanta.

23. An angiographic examination method for a patient, the method comprising:

generating quasi-coherent X-ray radiation;

detecting the quasi-coherent X-ray radiation via an X-ray image detector including a detector layer formed of a plurality of pixels in an analysis direction perpendicular to grating lines of a diffraction or phase grating arranged between the examination object and the X-ray image detector; wherein the detecting is based on an iterative readout process in which, a first plurality of subgroups of the plurality of pixels are read out while a second plurality of subgroups of the plurality of pixels are not read, each of the second plurality of subgroups being interposed between two of the first plurality of subgroups, each of the first and second plurality of subgroups including at least one of the plurality of pixels, the first and second plurality of subgroups change in each iteration of the readout process compared to other iterations of the readout process, and the readout process is iteratively performed until all of the plurality of pixels are read out; and performing image processing upon completion of the readout process.

24. The angiographic examination method of claim 23, wherein the iterative readout process is a non-destructive readout process.

* * * * *